United States Patent
Ng et al.

[11] Patent Number: 5,820,559
[45] Date of Patent: Oct. 13, 1998

[54] COMPUTERIZED BOUNDARY ESTIMATION IN MEDICAL IMAGES

[76] Inventors: Wan Sing Ng, Blk 827, Jurong West Street 81 #06-278, Singapore, Singapore, 2264; Ming Yeong Teo, 612 Ang Mo Kio Avenue 4, #04-1143, Singapore, Singapore, 560612

[21] Appl. No.: 821,641

[22] Filed: Mar. 20, 1997

[51] Int. Cl.$^6$ .................................................. A61B 8/00
[52] U.S. Cl. ................................. 600/439; 600/443
[58] Field of Search ........................ 606/15, 20–21, 606/39–41, 159, 169; 601/2, 3; 600/439, 443, 461–463, 470; 382/6

[56] References Cited

U.S. PATENT DOCUMENTS

| | | | |
|---|---|---|---|
| 5,178,148 | 1/1993 | LaCostel et al. | 600/439 |
| 5,201,731 | 4/1993 | Hakky | 606/15 |
| 5,224,175 | 6/1993 | Gouge et al. | 382/6 |
| 5,398,690 | 3/1995 | Batten et al. | 600/439 X |
| 5,411,026 | 5/1995 | Carol | 600/439 |
| 5,454,371 | 10/1995 | Fenster et al. | 128/916 |
| 5,531,742 | 7/1996 | Barken | 606/21 |
| 5,647,868 | 7/1997 | Chinn | 606/21 |

*Primary Examiner*—Francis Jaworski
*Attorney, Agent, or Firm*—Sughrue, Mion, Zinn, Macpeak & Seas, PLLC

[57] ABSTRACT

A computerised boundary estimation technique (using prostate as an example) in medical images (ultrasound in particular), called Radial Bas-Relief. An imaging probe can be carried by a robot and shares the same reference frame as the robot. The prostate is scanned and the ultrasound images are fed into a computer which provides computational images processing. Such a method is employed to allow a quick and robust extract of the boundary of interest from transverse images taken transurethrally or transrectally.

8 Claims, 7 Drawing Sheets

FIG. 9 x-LATERAL INTERVAL
O-ENTRANCE POINT

COMPUTERIZED BOUNDARY ESTIMATION IN MEDICAL IMAGES

BACKGROUND OF THE INVENTION (a) Field of the Invention

The present invention generally relates to medical image processing, and more particularly, is concerned with intraoperative ultrasound scanning using Radial Bas-Relief (RBR) method for automated prostatectorny which provides a quick and robust extraction of the prostate boundary from images taken transurethrally or transrectally. In accordance with the present invention, this method can be employed to outline the prostate boundary area automatically. The results of the ultrasound image processing serve to automate the transurethral resection of the prostate.

(b) Description of the Prior Art

The progress of robotic surgery has become active in the past decade. In the 1990s, many surgical robots were developed and some were tested in clinical trials. The work on automated prostatectomy, an example of active robotic surgery, has been disclosed in the article, entitled "Robotic surgery—a first hand experience in TURP", *IEEE Engineering in Medicine and Biological magazine*, 12(1), pp120–125, March 1993, by Ng Wan Sing, Davies B. L. et al. In the Article, it is suggested that transurethral resection of the prostate is currently the most common method of relieving urinary outflow obstruction. This procedure involves the introduction of a cutter through the urethra, and extending the cutter into the prostate, where successive cuts can be performed to remove the adenoma, which is the enlargement of the prostate gland. As part of the mate aging process, enlargement of the prostate gland inevitably occurs, which causes obstruction to urinary outflow. The adenoma is proximal to the verumontanum and it must be removed surgically so as to relieve the obstruction. A device, known as "SARP"—Surgical Assistant Robot for Prostatectomy, is employed to perform the automated prostatectomy. SARP is an unusual example in which a specific safety frame of suitable kinematic configuration is developed to generate multiple conical or barrel shape cavities in the prostate. Unlike many other systems, SARP is an active surgical robot. The advantages derived from the robotic operation of SARP are the positional certainty and time saving. These features are important in an operation because (i) the certainty in position ensures that resections will not unknowingly be directed into unwanted area, and position certainty is achieved by either internal or external sensors (Example of internal sensor can be optical encoder mounted with each joint motor, and example of external sensor can be optical/magnetic tracking device); and (ii) a reduction of time can be achieved by the removal of, for instance, repeated checking of some important landmarks or features, careful survey of tissue texture as new ones unfold as a result of cutting; and continuous mental visualisation of the surrounding anatomy. (The time saving achieved by high motor speeds will directly reduce the duration the patient being under anaesthetic and the amount of irrigant absorption.)

In respect of the automated prostatectomy system, the surgeon normally interacts with the following three components of the system: (1) the computer and its associated monitor display; (2) endoscope display unit; and (3) a bank of switches and a light emitting diode display. In the automated prostatectomy system, in order to let the robot system see beyond the immediate environment provided by the endoscopic view, the ultrasound imaging is used intraoperatively with the robot system. The ultrasound probe, either the transurethral or transrectal type, is advanced to the bladder neck and then retracted precisely under regular steps. The transverse scans of the prostate are obtained in these steps. The prostate boundary is marked. The capsule/adenoma boundary, which is the demarcation between the capsule and the enlarged tissue, lies within the prostate boundary. The capsule/adenoma boundary touches the prostate boundary anteriorly and is somewhat away from it posteriorly.

Because the intervals between scans are known and the ultrasound probe axis is common among them, a 3-dimensional reconstruction can be performed. A 3-dimensional ultrasound system acquiring and displaying 3-dimensional volume data in real time is described and illustrated in "Merging Virtual Objects with the Real World: Seeing Ultrasound Imagery Within the Patient", by Michael Bajura, Henry Fuchs, and Ryutarou Ohbuchi, published in Computer Integrated Surgery, edited by R Taylor, published in 1996. This article discloses (1) algorithms for acquiring and rendering real-time ultrasound data with known positions and orientations tracked by external sensors, (2) creating a working virtual environment that acquires and displays 3-dimensional ultrasound data in real time, and (3) recovering structural information for volume rendering specifically from ultrasound data. Consequently, cutting strategy can be planned accordingly to maximise resection so that multiple conical or barrel shape cavities can be generated, leaving behind a definite amount of adenoma yet sufficient to obtain an acceptable post-operative performance.

Many imaging methods are available that can be assisted by the computer, such as CT, MRI and ultrasound. Compared to CT and MRI images or photographic images taken from microscopes, ultrasound images are more difficult to process due to the presence of sparkles, noise and poor resolution. Segmentation of ultrasound images to extract boundary information or other features such as tumours has been a topic that is much researched. However, ultrasound image has advantages over other modalities. For modalities such as CT and MRI, it is time consuming to obtain high-resolution image quickly. initial and maintenance costs are very high and they cannot be used conveniently and safely in the operating theatre without elaborate precautions. Currently, the transrectal ultrasound imaging procedure is highly manual and hence laborious. Because the scanning is done preoperatively, there is a big difficulty in registering pre-and intraoperative data when the robot is used on a patient. Ultrasound has been used in SARP because of its relatively low cost, the ease with which it can be easily introduced into the operating room, and because it has no unfavourable effects on the patient The ultrasound image and processing system employed by SARP is the B&K type 1846 scanner equipped with 7 MHz and 5.5 MHz probes. The image system is a diagnostic scanner and is used in SARP primarily for sizing the prostate. The sizing is accomplished by successive transverse scans of the prostate taken transrectally preoperatively. Continuous stacks of transverse scans are reconstructed on the IBM computer to form a 3-D model of the prostate.

To realise a quick boundary estimate of the prostate, including reconstructing a 3-dimensional model computationally and subsequent resection planning based on the model, the inventors of the present invention turned away from the conventional pixel by pixel analysis and introduced the method of Radial Bas Relief. Bas Relief is a darkroom technique used in photography. In the reference, "The step-by-step guide to photography", New York: Alfred A. Knopf, Inc., by Langford, M, the Bas Relief method used in photography is disclosed. In accordance with the present invention, the Radial Bas Relief (RBR) method has been found to be useful in estimating the prostate boundary or, for that matter, other organs. According to this method, a Bas-relief image is made by superimposing the positive onto the negative image, slightly out of register, and printing the images as one that looks like low relief sculptures, lighted from one side. The resulting image will be simplified into a pattern of lines and flat tones. This way, edges in the image can be highlighted.

SUMMARY OF THE INVENTION

The present invention is directed to a method of medical image (ultrasound in particular) processing that satisfies the precise sizing of the prostate (using prostate as an example). In accordance with the present invention, it also discloses a simple method to estimate the boundary of the prostate using the computer, which serves further to the procedure of the transurethral resection of the prostate. In accordance with the preferred embodiment of the present invention, the present method of ultrasound scanning for automated prostatectomy using a robotic system comprising a surgical robot having a head axis, a computer, a 4-axis motion controller, an ultrasound scanner, and an ultrasound probe (transurethral or transrectal type) which passes through the outersheath of a resectoscope being mounted to said surgical robot, comprises the steps of:

(a) engaging said resectoscope to said robot having being suspended on a counterbalance gantry at an undisturbed referenced position (called verumontanum);

(b) scanning for prostate on a patient by moving said head axis of said surgical robot having being mounted with said ultrasound probe;

(c) feeding the scanned images obtained in step (b) into said frame grabber and digitising said images to provide computational image processing; and (d) outlining the prostate by said computer.

In accordance with the present invention, the computerized estimation in ultrasound image using Radial Bas-Relief method comprises further steps of (a) inverting the ultrasound image of the prostate to obtain an inverted image;

(b) enlarging proportionally said inverted image in an orthogonal direction to obtain an enlarged image;

(c) adding said enlarged image of (f) to said ultrasound image obtained in claim 1 to result a Bas-relief image containing grey level now with edge information enhanced;

(d) binarising said Bas-relief image obtained in (g) to remove the grey level thereof;

(e) dilating and eroding the binarised image of (h) to obtain a smoother outline of the prostate boundary contour, and (f) thinning the dilated or eroded image of (i) to provide a skeletonised outline, whereby the capsule boundary is thus determined from the prostate boundary.

Accordingly, it is an object of the present invention to provide a method of ultrasound image processing, wherein the resectoscope for operation and the ultrasound probe for scanning are carried by the robot so that they share the same reference frame as the robot.

It is another object of the present invention to provide a method of ultrasound image processing for automated prostatectomy, wherein the elaborated patient registration (the matching of pre- and intraoperative data) is avoided by having a common reference for the imaging system and the robot.

Yet it is another object of the present invention to provide a method of ultrasound image processing for automated prostatectomy, wherein the time taken to capture and process each scan is short.

Yet it is another object of the present invention to provide a method of ultrasound image processing for automated prostatectomy, wherein the setup of the robotic procedure is greatly simplified by having a counterbalance gantry.

These and other features, aspects, and advantages of the present invention will become better understood with regard to the following description, appended claims, and accompanying drawings where:

DESCRIPTION OF THE PREFERRED EMBODIMENT

Figure 1:
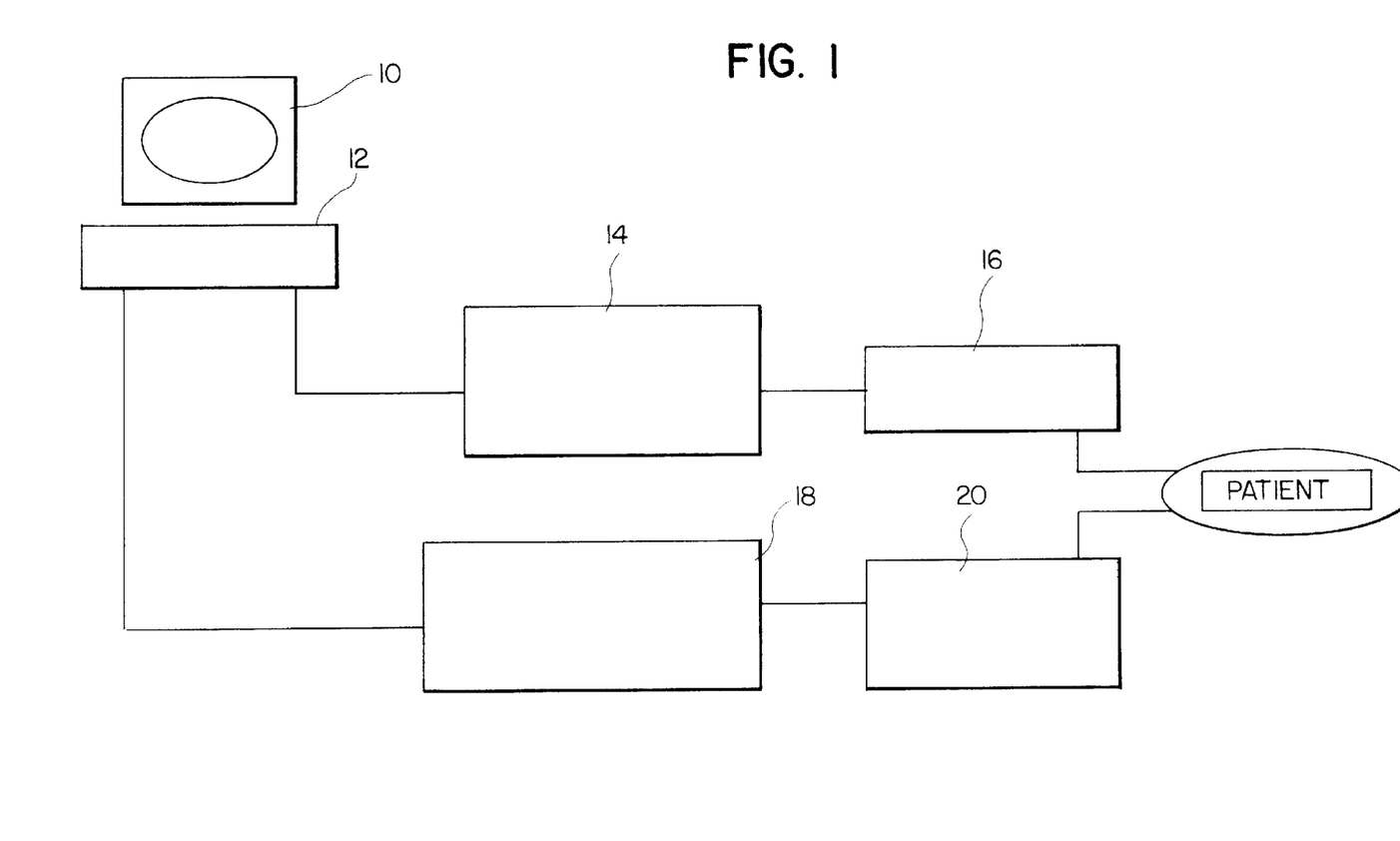
FIG. 1 illustrates the arrangement of the devices for the computer assisted ultrasound imaging in accordance with the present invention.
Figure 2:
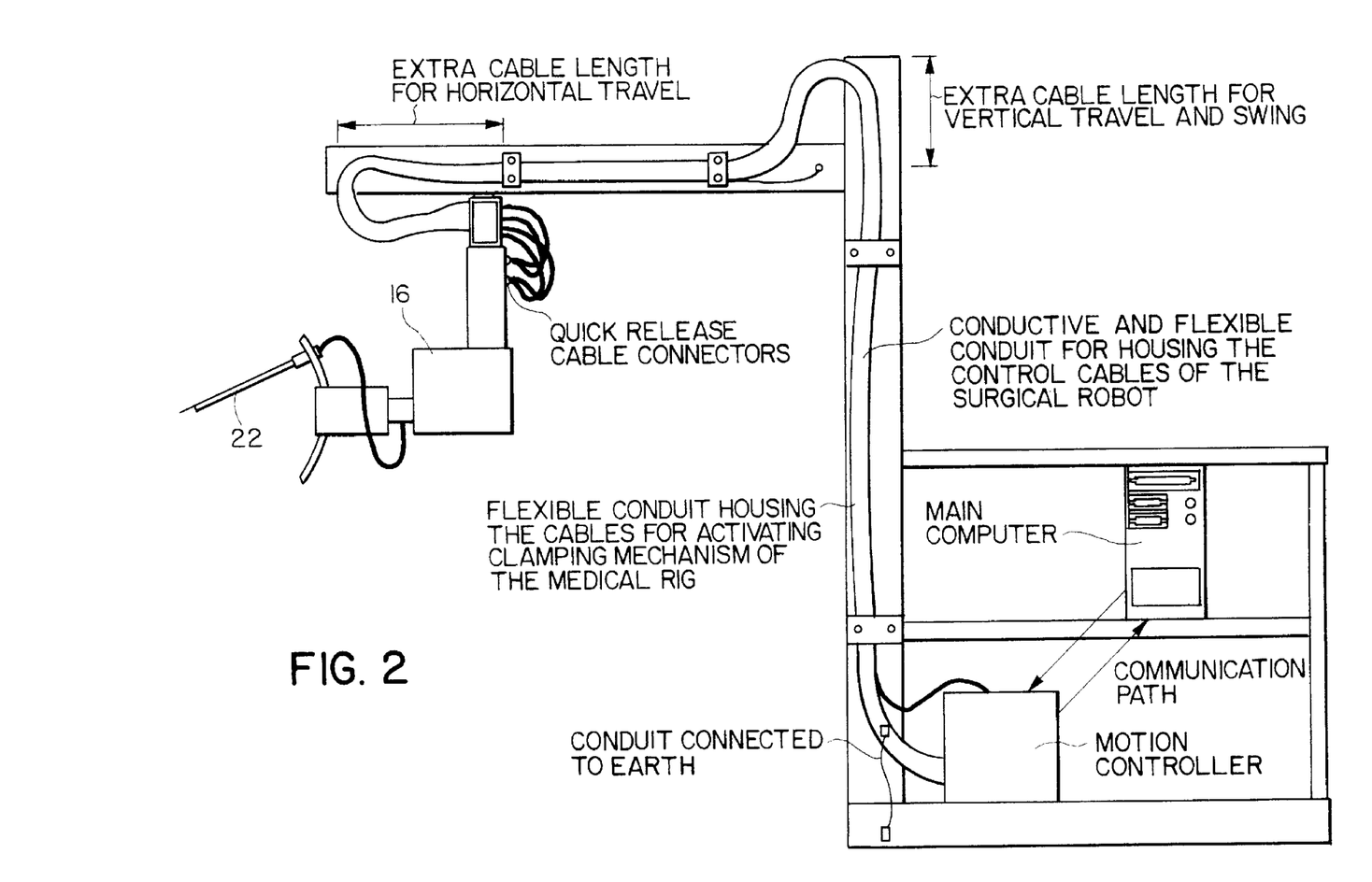
FIG. 2 illustrates a layout of Surgeon Assistant Robot for selected Urological Disorders in accordance with the present invention.

Referring to FIG. 1, there is shown a layout of the computer assisted ultrasound imaging system, which is known as Surgeon Assistant Robot for selected Urological Disorders, or "SARUD". In accordance with the present invention, the system comprises a personal computer 10 a mother board equipped with a high speed frame grabber (12) with hardware implemented image processing functions, such as inversion, addition, and scaling, a 4-axis motion controller 14, a surgical robot 16, an ultrasound scanner 18, and a transrectal or a transurethral probe 20. The ultrasound scanner 18 can be selected either from the Bruel and Kjoer type 1846 scanner or the Krez Combinson 430. In the preferred embodiment of the present invention, the robot 16, which is suspended on a counterbalance, can hold the transrectal ultrasound probe or transurethral ultrasound probe 20. The 4-axis motion controller 14 provides four axes of movement, namely the head travel axis (a linear axis), a ring axis (rotational, an arch axis (rotational) and a pivot length drive axis (linear). The axes are mounted on the other in this order. FIG. 2 shows schematically the layout of the robot 16 in accordance with the present invention. The transurethral probe 20 passes through the outer sheath of the resectoscope 22, as shown in FIG. 2. An adaptor (not shown) is used to provide rigid mounting of the resectoscope 22 to the robot 16. A different adaptor (not shown) with an offset from the central axis of the resectoscope 22, is used for the transrectal probe (not shown). As shown in FIG. 2, when the reference position (an anatomical landmark called verumontanum) is found endoscopically and undisturbed, the resectoscope 22 is engaged to the robot 16. The robot 16 is suspended on a counterbalance gantry and a specially designed tool holder is used for the mounting. Before an operation is performed on a patient, the prostate is scanned using either the transurethral ultrasound scanning with SARUD or the transrectal ultrasound scanning with SARUD. Only the head axis of the robot 16 is moved to carry the rest of the robot arm, including the horizontally mounted ultrasound probe 20 and its adaptor (not shown) so that a plurality numbers of transverse sections of the gland will be scanned, starting from the bladder neck toward the verumontanum.

The length of the prostate, measured from the verumontanum to the bladder neck, will have been obtained endoscopically by advancing the head of the robot 16 under the manual control before the scan takes place. The above method takes advantages of the tool holder of the robot 16 to mount both the resectoscope 22 for the operation and the ultrasound probe 20 for scanning, one at a time. The outer sheath of the resectoscope 22 remains in the patient's urethra throughout the scanning and resection procedure. This ascertains that the image reference axis falls in line with the ring axis and is parallel to the head axis of the robot 16. As a result of the same axes being used to do resections, no registration or pre- and intra-operative data is necessary. The scanning is done intra-operatively and the image reference frame is the same as that of the robot 16.

When scanning is completed, a cutting element (not shown) is introduced and attached onto the outer sheath of the resectoscope 22, without disturbing either the target position or the robot 16 which is mounted sufficiently rigidly in space using the counterbalance gantry and structure.

The ultrasound images, during scanning, are fed into the frame grabber (12) which digitises them to enable computational image processing. Every transverse scan is captured, displayed on the monitor and stored away eventually for documenting purposes.

All prostate boundary can be outlined by the surgeon or a trained person (who controls and supervises the operation through the computer) by the use of a light pen, or by introducing an automatic capsule delineation program to do the outlining.

It is important to reduce the time of a TURP so that the patient will not be subjected to prolonged anaesthesia. Also, the resulting reduction in irrigant absorption will avoid complications like breathing difficulty and dilution of blood. Furthermore there will also be less blood loss. To manually outline the capsule boundary, it can be very time consuming, especially when the surgeon is not experienced in reading sonographs. Depending on the length of the prostate and the accuracy and resolution required, there can be easily over ten transverse sections, each of which requires the capsule boundary to be delineated. Since it is intended that the robot 16 should complete the entire operation in less than 30 minutes, it becomes highly desirable that the scanning should take not more than 5 to 8 minutes to complete, leaving enough time for resections.

In accordance with the present invention, it is our desire to look for an automated solution for the outlining task with the help of the computer. A novel variation to a method called Bas-relief, which is known in the photography technology, is developed that allows a quick and robust extraction of the prostate boundary from transverse images taken transurethrally or transrectally. Bas-relief is a process by which a third dimensional effect may be added to a print. In order to give a dean picture in the computer memory, unwanted branches detected along with the desired contour are eliminated. Unavailable information needed to close the prostate contour will be extrapolated based on scans in the neighbourhood sections.

Figure 3:
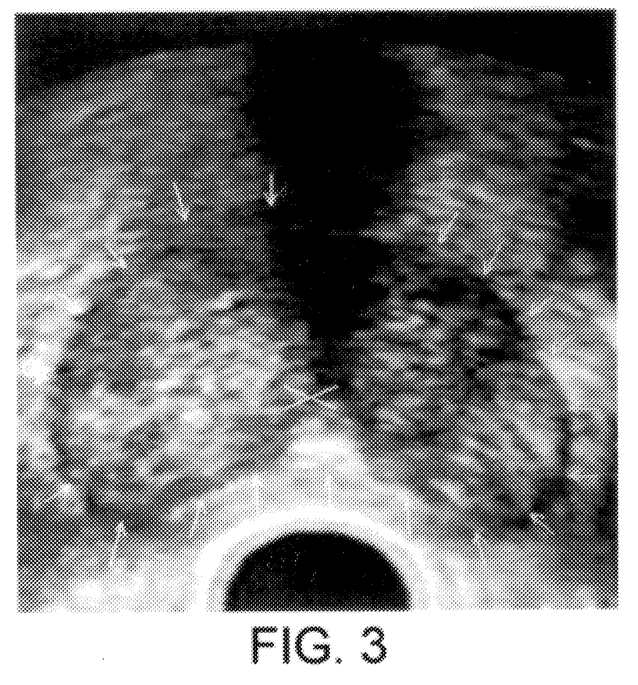
FIG. 3 illustrates a typical transverse ultrasound scan of the prostate, taken transrectally in accordance with the present invention.
Figure 4:
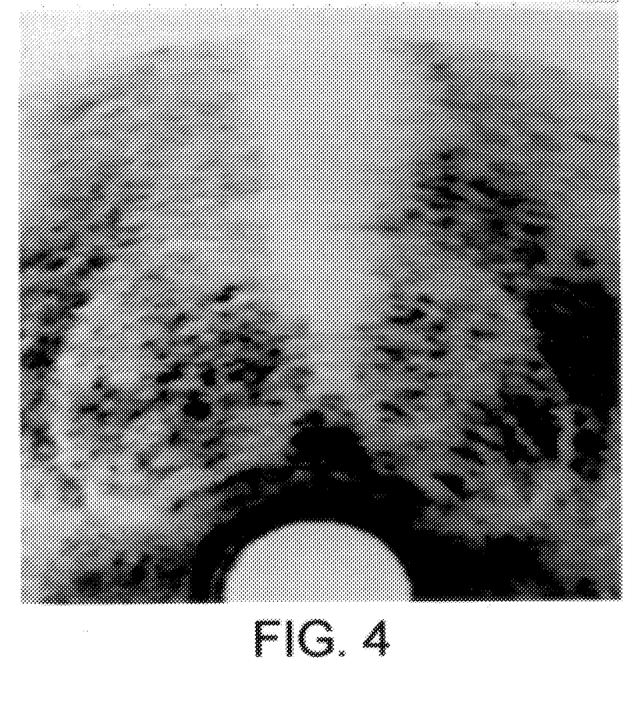
FIG. 4 illustrates a simple inversion image of FIG. 3 in accordance with the present invention.
Figure 5:
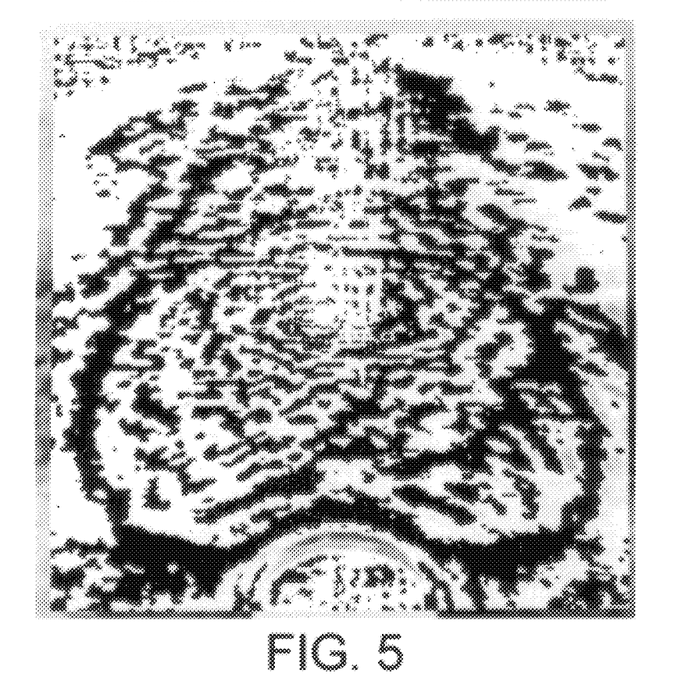
FIG. 5 illustrates a picture obtained by adding the image of FIG. 4 to FIG. 3 in accordance with the present invention.
Figure 6:
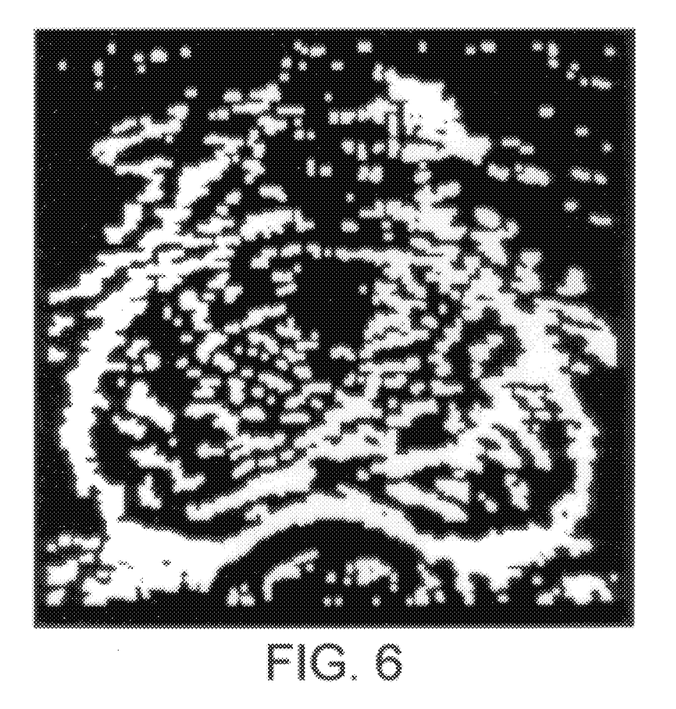
FIG. 6 illustrates a binarised image of FIG. 5 in accordance with the present invention.
Figure 7:
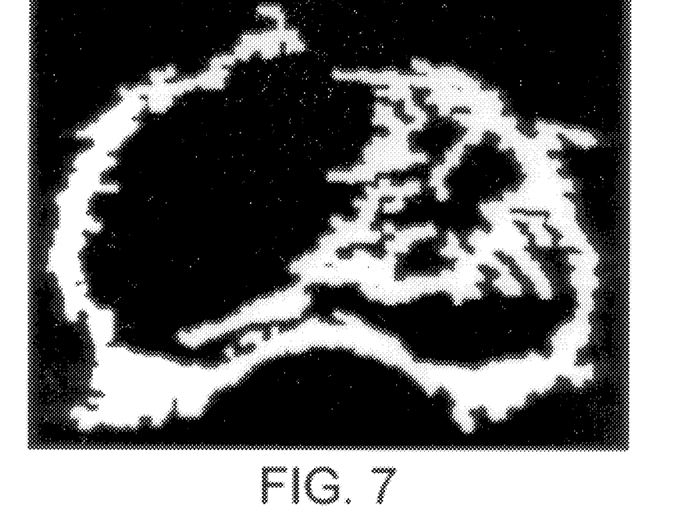
FIG. 7 illustrates a smoothed image of FIG. 6 by dilation and erosion in accordance with the present invention.
Figure 8:
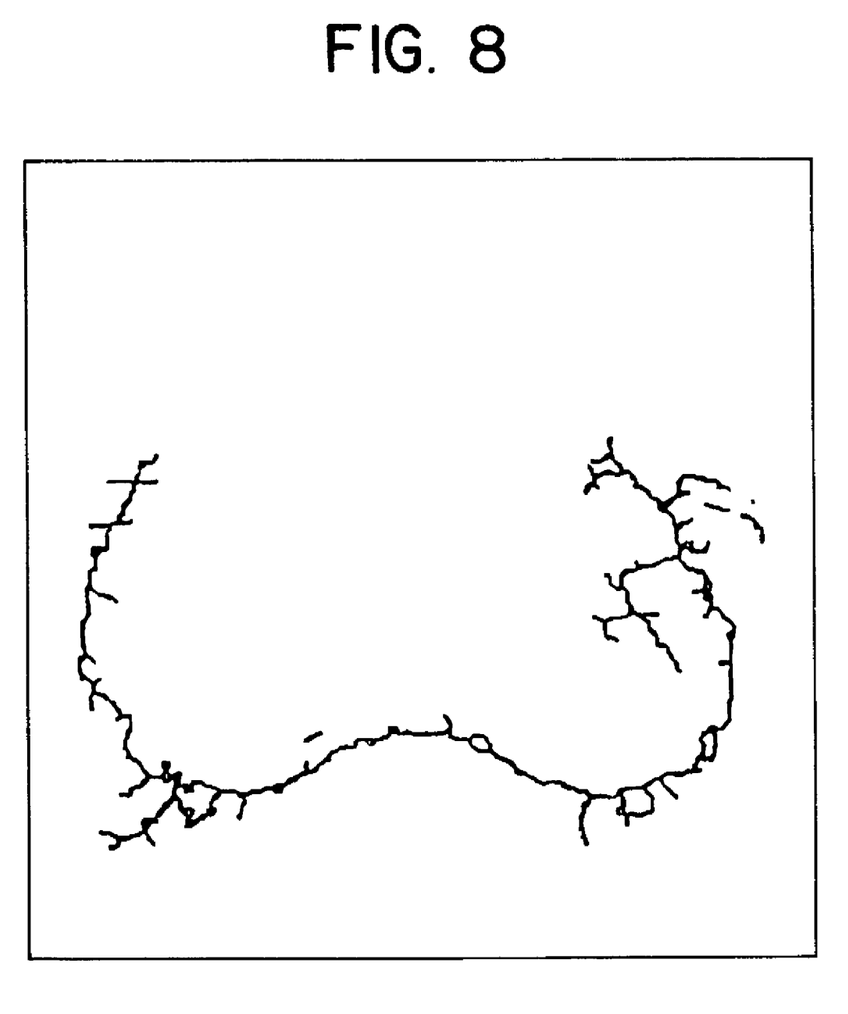
FIG. 8 illustrates the image of an extracted capsule boundary in accordance with the present invention.

FIG. 3 shows a typical transverse ultrasound scan of the prostate, taken transrectally. The prostate boundary is marked with white arrows. The capsule/adenoma boundary, demarcation between the capsule and the enlarged tissue ("the adenoma") lies within the prostate boundary. The adenoma is to be removed surgically. As shown in the Figure, it is obvious that there is an object, eg. stone, of sufficient density at the location marked "X". FIG. 4 shows an inverted image of the ultrasound image of FIG. 3. The inverted image is enlarged proportionally in the orthogonal directions. The enlarged inversion is then added to the original image. The result of the addition is shown in FIG. 5. It can be seen in FIG. 5 that the band around the edges is due to the inversion being larger than the original image. This is the result of the RBR method. Using a very basic digital image operation, called binarisation, the image is further processed to remove the grey level. The binarised image is shown in FIG. 6. In order to obtain a smoother outline of the capsule contour, the binarised image is subjected to the so-called "dilate" and "erode" operations. These operations patch up little "holes" in the contour band (as shown in FIG. 7) to facilitate the next operation known as skeletonisation, or thinning. FIG. 8 shows the extracted capsule boundary after thinning. The "dilate" and "erode" operations, and the skeletonisation operation can be accomplished by the use of an image processing software package, such as "Optimas", which is available from Bioscan Inc.

Figure 9:
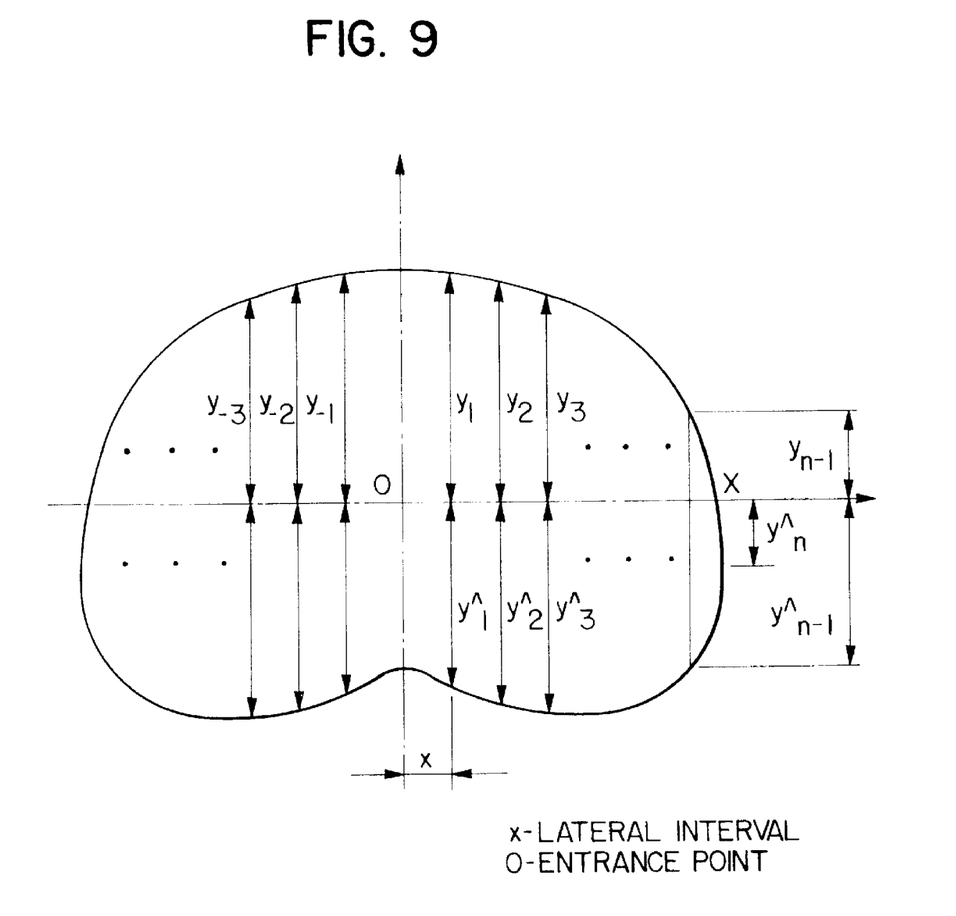
FIG. 9 illustrates the X-Y coordinates formulation on a typical capsule/adenoma boundary in accordance with the present invention.

The object marked "X" will generate echoes which crossed out all useful information in the radial path. This can be seen in FIG. 8 as short branches (sometimes long ones) that deviate from the desired boundary. Extrapolations and branch-elimination of some kind will have to be applied so as to obtain the contour as shown in FIG. 9. In addition, the overall dimensions will have to be scaled down by a suitable amount to compensate for the enlargement of the inversion. In accordance with the present invention, Radial Bas Relief can benefit from conventional ways of image preprocessing such as grey level normalisation, etc. (which are pixel by pixel processing within a defined region of interest). The Radial Bas Relief will also not work without a robotic platform.

It is readily apparent that various changes and modifications may be made to the method of medical imaging. Such changes and others may be made without departing from the spirit and scope of the invention which is set forth in the claims appended hereto.

We claim:

1. A method of producing a computerized boundary estimation in medical images using a Radial Bas-Relief technique, and utilizing a surgical robot having a head axis, a computer equipped with a frame grabber, a 4-axis motion controller, an ultrasound scanner, and one of a transurethral and a transrectal ultrasound probe which passes through an outer/sheath of a resectoscope mounted to said surgical robot, said method comprising the steps of:

(a) engaging said resectoscope to said robot suspended on a counterbalance gantry at an undisturbed reference position (verumontanum); and (b) scanning for a target organ on a patient by moving said head axis of said surgical robot mounted with said ultrasound probe;

wherein scanned images obtained in (b) are fed into said frame grabber, and images of said target organ are then digitized to enable image processing and boundary estimation outlining by said computer.

2. A computerized boundary estimation in medical images using method as set forth in claim 1, further comprising the steps of:

(c) inverting the medical image of the target organ to obtain an inverted image;

(d) enlarging proportionally said inverted image in an orthogonal direction to obtain an enlarged image;

(e) adding said enlarged image of (d) to said medical image obtained in claim 1 to result in a Bas-relief image containing grey level now with edge information enhanced;

(f) binarising said Bas-relief image obtained in (e) to remove the grey level thereof;

(g) dilating and eroding the binarised image of (f) to obtain a smoother outline of the target organ boundary contour; and (h) thinning the dilated or eroded image of (g) to provide a skeletonised outline.

3. A computerized boundary estimation method as set forth in claims 1 or 2, wherein the target organ boundary is outlined by the use of a light pen on the monitor screen.

4. A computerized boundary estimation method as set forth in claim 3, wherein the target organ is the prostate.

5. A computerized boundary estimation method as set forth in claims 1 or 2, wherein the target organ boundary is outlined by an automatic capsule delineation program.

6. A computerized boundary estimation method as set forth in claim 5, wherein the target organ is the prostate.

7. A computerized boundary estimation method as set forth in claims 1 or 2, wherein a cutting element is introduced and attached onto the outer sheath of the resectoscope.

8. A computerized boundary estimation method as set forth in claims 1 or 2, wherein the target organ is the prostate.

* * * * *